United States Patent
Yeo et al.

(10) Patent No.: US 10,228,383 B2
(45) Date of Patent: Mar. 12, 2019

(54) TEST APPARATUS AND CONTROL METHOD THEREOF

(71) Applicant: SAMSUNG ELECTRONICS CO., LTD., Suwon-si (KR)

(72) Inventors: Yeong Bae Yeo, Seoul (KR); Sil Park, Gwangmyeong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 162 days.

(21) Appl. No.: 15/361,134

(22) Filed: Nov. 25, 2016

(65) Prior Publication Data

US 2017/0227407 A1 Aug. 10, 2017

(30) Foreign Application Priority Data

Feb. 5, 2016 (KR) ........................ 10-2016-0014593

(51) Int. Cl.

| | |
|---|---|
| *A61B 5/00* | (2006.01) |
| *G01N 21/01* | (2006.01) |
| *G01N 21/25* | (2006.01) |
| *G01N 21/78* | (2006.01) |
| *G01N 33/49* | (2006.01) |
| *G01N 35/00* | (2006.01) |

(Continued)

(52) U.S. Cl.
CPC ....... *G01N 35/00584* (2013.01); *G01K 11/16* (2013.01); *G01N 21/251* (2013.01); *G01N 21/78* (2013.01); *G01N 33/49* (2013.01); *A61B 5/0261* (2013.01); *G01N 21/75* (2013.01); *G01N 2021/6439* (2013.01); *G01N 2201/1211* (2013.01)

(58) Field of Classification Search
CPC ........ G01K 11/16; G06K 11/12; G06K 11/16; G01N 35/00584; G01N 21/78; G01N 21/75; G01N 2021/6439; G01N 21/251; G01N 2201/1211; G01N 33/49; A61B 5/0261

See application file for complete search history.

(56) References Cited

U.S. PATENT DOCUMENTS

2010/0007886 A1* 1/2010 Okabayashi ........... G01N 21/31
356/409
2010/0214373 A1* 8/2010 Carr ....................... B41M 3/142
347/73

(Continued)

*Primary Examiner* — Jennifer Wecker
(74) *Attorney, Agent, or Firm* — Sughrue Mion, PLLC

(57) ABSTRACT

A test apparatus for measuring the temperature of a reactor using a thermochromic pigment, and a method for controlling the test apparatus are disclosed, based on a technology for irradiating light of different wavelengths on a thermochromic pigment accommodated in a reactor and estimating temperature of the reactor using a difference between absorbance values corresponding to the light of the different wavelengths. The test apparatus includes at least one light emitter configured to irradiate light of different wavelengths onto a chamber included in the reactor, a light receiver configured to receive the light that propagates through the chamber, and a controller configured to measure absorbance values of the thermochromic pigment in correspondence to the different wavelengths of the light, to calculate a difference between the measured absorbance values, and to determine a temperature of the reactor in correspondence to the calculated difference between the absorbance values.

17 Claims, 15 Drawing Sheets

(51) Int. Cl.
*G01K 11/16* (2006.01)
*G01N 21/75* (2006.01)
*A61B 5/15* (2006.01)
*G01N 21/64* (2006.01)
*A61B 5/026* (2006.01)

(56) References Cited

U.S. PATENT DOCUMENTS

2011/0070603 A1* 3/2011 Kim .................... G01N 33/487
                                                    435/29
2016/0243334 A1* 8/2016 Da Silva ............ A61M 25/0111

* cited by examiner (A) TEST APPARATUS A (B) TEST APPARATUS B

TEST APPARATUS AND CONTROL METHOD THEREOF

CROSS-REFERENCE TO RELATED APPLICATION

This application claims priority from Korean Patent Application No. 10-2016-0014593, filed on Feb. 5, 2016 in the Korean Intellectual Property Office, the disclosure of which is incorporated herein by reference in its entirety.

BACKGROUND

1. Field

Exemplary embodiments relate to a test apparatus for measuring the temperature of a reactor using a thermochromic pigment, and a method for controlling the test apparatus.

2. Description of the Related Art

For vitro diagnosis, immunoassay, a clinical-chemical test, and/or other tests are performed on a patient's samples. The immunoassay and the clinical-chemical test are very important in diagnosing the patient's state, treating the patient, and determining a prognosis.

The vitro diagnosis is performed generally in a hospital examination room or a laboratory. Recently, in order to analyze samples quickly and perform vitro diagnosis at any place in various fields, such as environmental monitoring, food inspection, medical diagnosis, etc., a need for miniaturization of a vitro diagnostic apparatus is increasing.

In particular, in a medical diagnosis field, dependency on a Point-Of-Cure (POC) blood analyzer that includes a disposable cartridge is increasing, and accordingly, studies into a compact POC blood analyzer which facilitates the performance of rapid, accurate blood tests are actively conducted all over the world.

Since the results of a blood test are greatly influenced by temperature, it is important to maintain a reagent and test medium at a constant temperature. Accordingly, for an accurate blood test (a clinical-chemical test or an immune serum test), it is necessary to accurately control the temperature of a reagent cartridge.

SUMMARY

Therefore, it is an aspect of one or more exemplary embodiments to provide a technique for irradiating light of different wavelengths on a thermochromic pigment accommodated in a reactor and estimating a temperature of the reactor by using a difference between absorbance values corresponding to the light of the different wavelengths, and more particularly, a test apparatus for minimizing an error in temperature estimation due to mechanical deviation, and a method for controlling the test apparatus.

Additional aspects of the exemplary embodiments will be set forth in part in the description which follows and, in part, will be apparent from the description, or may be learned by practice of the exemplary embodiments.

In accordance with one aspect of one or more exemplary embodiments, a test apparatus for measuring temperature of a reactor which includes a chamber in which a thermochromic pigment is accommodated, includes: at least one light emitter configured to irradiate light of different wavelengths onto the chamber included in the reactor; a light receiver configured to receive the light of the different wavelengths that propagates through the chamber; and a controller configured to measure absorbance values of the thermochromic pigment in correspondence to the different wavelengths of the light received by the light receiver, to calculate at least one difference between a respective pair of the measured absorbance values, and to determine the temperature of the reactor based on the calculated at least one difference.

The light emitter may irradiate light of a first wavelength and light of a second wavelength, and the second wavelength may be longer than the first wavelength.

The controller may measure a first absorbance value of the thermochromic pigment with respect to the irradiated light of the first wavelength, and the controller may measure a second absorbance value of the thermochromic pigment with respect to the irradiated light of the second wavelength.

The controller may calculate a difference between the first absorbance value and the second absorbance value.

The controller may determine the temperature of the reactor based on the calculated difference between the first absorbance value and the second absorbance value.

When the temperature of the reactor is lower than a predetermined temperature, the controller may heat the reactor until the temperature of the reactor reaches the predetermined temperature.

The test apparatus may further include a heater configured to heat the reactor.

The test apparatus may further include a memory configured to store data about the temperature of the reactor corresponding to the calculated at least one difference between the absorbance values.

The controller may heat the reactor until the temperature of the reactor is higher than the predetermined temperature, and when the temperature of the reactor becomes higher than the predetermined temperature, the controller stops heating the reactor.

In accordance with another aspect of one or more exemplary embodiments, a method for controlling a test apparatus includes: irradiating light of different wavelengths onto a chamber provided in a reactor; receiving the light of the different wavelengths that propagates through the chamber; measuring absorbance values of the thermochromic pigment in correspondence to the different wavelengths of the received light; calculating at least one difference between a respective pair of the measured absorbance values; and determining a temperature of the reactor based on the calculated at least one difference.

The irradiating of the light of the different wavelengths may include irradiating light of a first wavelength and light of a second wavelength, the second wavelength being longer than the first wavelength.

The measuring of the absorbance values of the thermochromic pigment may include: measuring a first absorbance value of the thermochromic pigment in correspondence to the irradiated light of the first wavelength; and measuring a second absorbance value of the thermochromic pigment in correspondence to the irradiated light of the second wavelength.

The calculating of the at least one difference between the measured absorbance values may include calculating a difference between the first absorbance value and the second absorbance value.

The determining of the temperature of the reactor may include determining the temperature of the reactor based on the calculated difference between the first absorbance value and the second absorbance value.

The method for controlling a test apparatus may further include when the temperature of the reactor is lower than a predetermined temperature, heating the reactor until the temperature of the reactor reaches the predetermined temperature.

The method for controlling a test apparatus may further include heating the reactor.

The method for controlling a test apparatus may further include heating the reactor until the temperature of the reactor is higher than the predetermined temperature, and transmitting a control signal for stopping heating the reactor when the temperature of the reactor becomes higher than the predetermined temperature.

In accordance with one aspect of one or more exemplary embodiments, a reactor includes: a reaction chamber in which a sample reacts with a reagent; a pigment chamber in which a thermochromic pigment is accommodated; and identification information including information about a temperature of the reactor.

The identification information may include at least one from among a barcode, a Quick Response (QR) code, text data, a data matrix, a recognition pattern, Near Field Communication (NFC), and Radio Frequency Identification (RFID), including information about temperature of the reactor.

The thermochromic pigment may be one from among a powder, a slurry, a master batch, a film, and a strip type.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
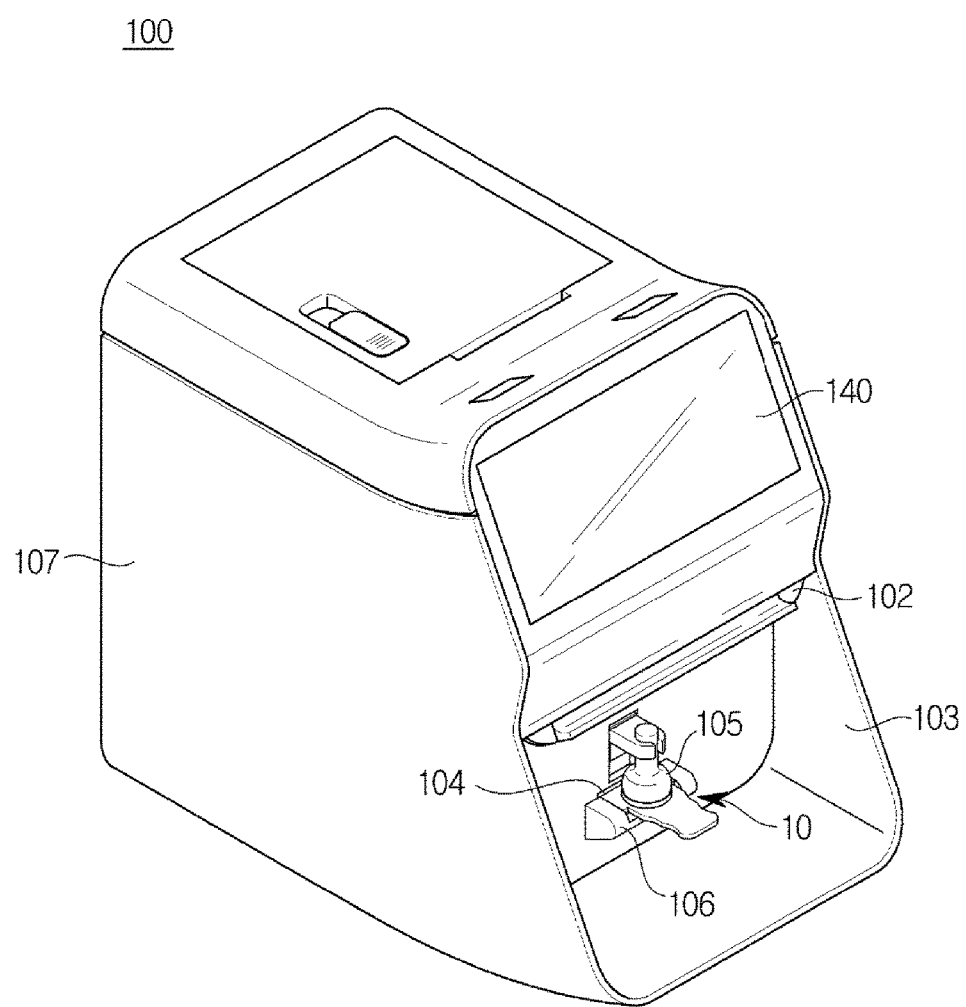
FIG. 1 is a perspective view showing the outer appearance of a test apparatus, according to an exemplary embodiment.

Advantages and features of the present disclosure and a method of achieving the advantages and features will be apparent by referring to exemplary embodiments described below in connection with the accompanying drawings. However, the present disclosure is not restricted by these exemplary embodiments, but can be implemented in many different forms. The present exemplary embodiments are provided to complete the disclosure of the present inventive concept and to allow those having ordinary skill in the art to understand the scope of the present disclosure. The present disclosure is defined by the category of the claims. Like reference numerals refer to like elements throughout this specification.

Terms used in this specification will be briefly described, and the exemplary embodiments will be described in detail.

Although general terms being widely used with respect to the exemplary embodiments were selected as terminology to be used in the present disclosure while considering the functions of the exemplary embodiments, they may vary according to intentions of one of ordinary skill in the art, judicial precedents, the advent of new technologies, and the like. Terms arbitrarily selected by the applicant of the present disclosure may also be used in a specific case. In this case, their meanings need to be given in the detailed description of the present disclosure. Hence, the terms must be defined based on the meanings of the terms and the contents of the entire specification, not by simply stating the terms themselves.

It will be understood that when the terms "includes," "comprises," "including," and/or "comprising," when used in this specification, specify the presence of stated elements and/or components, but do not preclude the presence or addition of one or more elements and/or components thereof. As used herein, the terms "part", "module", or "unit" refers to a unit that can perform at least one function or operation, and may be implemented as a software or hardware component such as a Field Programmable Gate Array (FPGA) or an Application Specific Integrated Circuit (ASIC). However, the term "part", "module" or "unit" is not limited to software or hardware. The "part", "module", or "unit" may be configured in an addressable storage medium, or may be configured to run on at least one processor. Therefore, as an example, the "part", "module", or "unit" includes: components such as software components, object-oriented software components, class components, and task components; processors, functions, attributes, procedures, sub-routines, segments of program codes, drivers, firmware, microcodes, circuits, data, databases, data structures, tables, arrays, and variables. Functions provided in the components and the "part", "module", or "unit" may be integrated into the smaller number of components and the "part", "module", or "unit", or may be sub-divided into additional components and an additional "part", "module", or "unit".

Hereinafter, exemplary embodiments will be described in detail with reference to the accompanying drawings so that the exemplary embodiments may be readily implemented by those skilled in the art. However, the present disclosure can be implemented in different forms, and is not limited to the exemplary embodiments which will be described below. In the drawings, parts irrelevant to the description are omitted for the simplicity of explanation.

In this specification, the term "user" may be a medical specialist, such as an emergency technician, a doctor, a nurse, a medical technologist, a radiological technologist, or may also be an engineer who repairs medical equipment, although not limited to the above-mentioned persons.

Also, a test apparatus according to an exemplary embodiment which will be described below is assumed to be a vitro diagnostic apparatus, although not limited to this.

Also, a reactor according to an exemplary embodiment which will be described below is assumed to be a cartridge that can accommodate a sample, a reagent, a thermochromic pigment, etc. The thermochromic pigment is a reversible, thermo-photosensitive material whose color changes according to temperature, and also called a thermochromic material. The thermochromic pigment will be described below.

Needs for rapid and accurate Point-Of-Care (POC) testing in various fields, such as environmental monitoring, food inspection, medical diagnosis, etc., are increasing. Particularly, in a medical diagnosis field, dependency on a POC blood analyzer using a disposable cartridge is increasing, and accordingly, studies into a compact POC blood analyzer enabling rapid, accurate blood tests are actively conducted all over the world. In a blood analyzer based on Lab-on-a-chip or Lab-on-a-disc for field inspection, miniaturization and supporting simultaneous tests for multiple items are very important factors. Accordingly, a Lab-on-a-chip or Lab-on-a-disc cartridge needs to include a plurality of detection chambers, and an optical detection apparatus (a test apparatus) also should be able to scan and measure such a plurality of detection chambers.

Since clinical-chemical responses and immune serum responses are very sensitive to temperature in blood analysis using such a vitro diagnostic apparatus, it is important to maintain a reagent and test medium at a constant temperature. Accordingly, the vitro diagnostic apparatus can include a temperature sensor, a heater, etc. to control the temperature of the cartridge. However, due to mechanical deviation caused by the heater, the temperature sensor, a controller, etc., temperature differences may occur between a plurality of test apparatuses, and the temperature differences may cause differences between the results of tests performed by the test apparatuses. Therefore, means for accurately measuring and correcting temperature differences between the plurality of test apparatuses is needed.

According to a test apparatus and a control method thereof which will be described below with reference to the accompanying drawings, when a temperature of a cartridge is estimated based on an absorbance value of a thermochromic pigment, the temperature of the cartridge can be accurately and precisely calculated, regardless of scattering of light that propagates through the thermochromic pigment and the mechanical deviation of the test apparatus. Also, it is possible to minimize an absorbance error according to the wavelength of light irradiated by the test apparatus.

Figure 2:
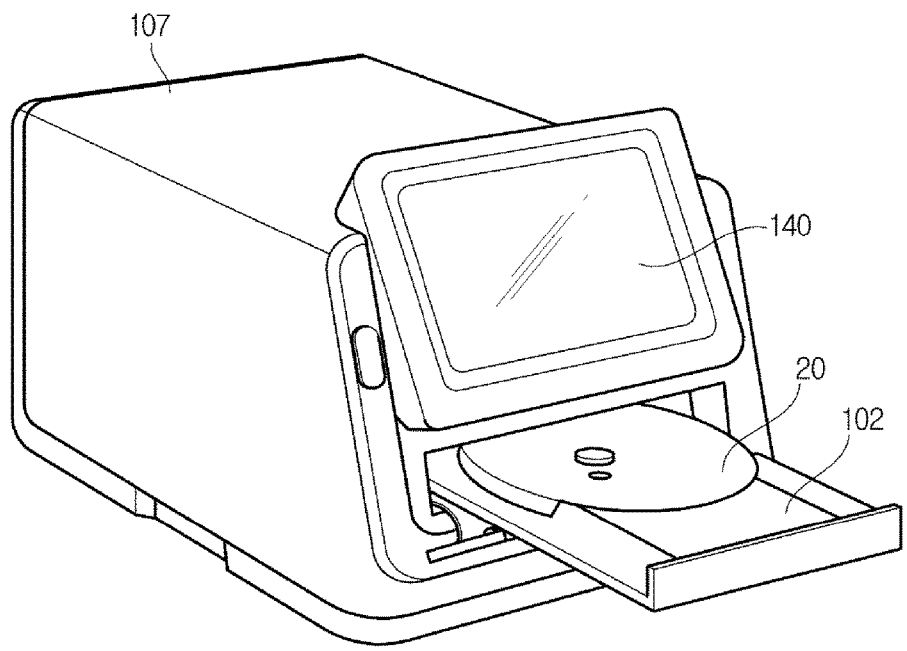
FIG. 2 is a perspective view showing the outer appearance of a test apparatus, according to another exemplary embodiment.
Figure 3:
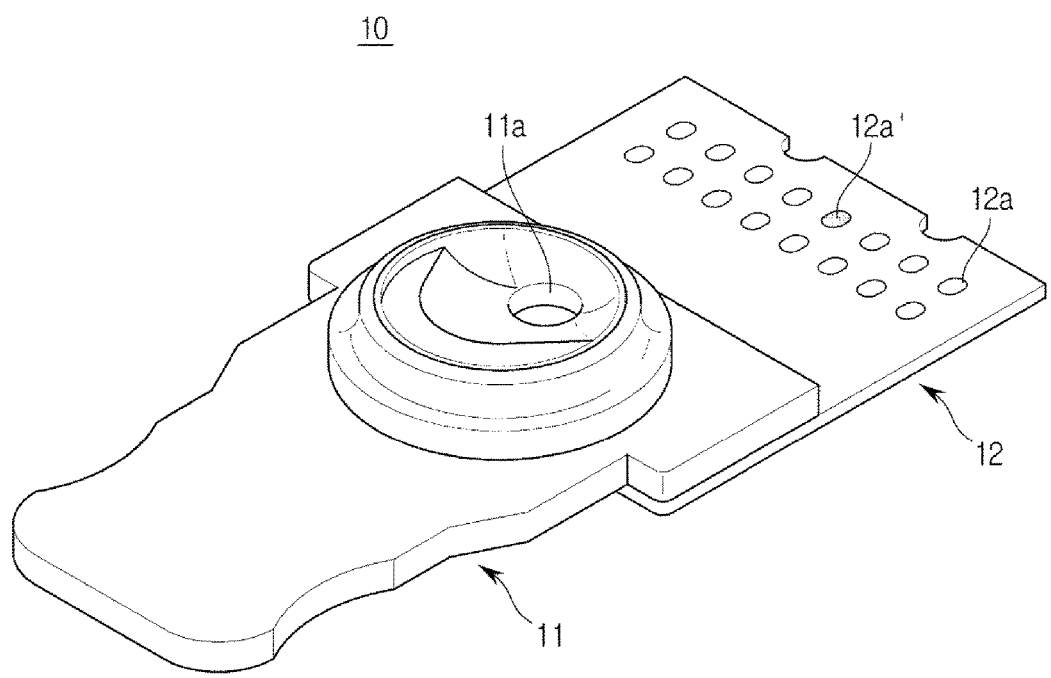
FIG. 3 is a perspective view showing the outer appearance of a reactor inserted into the test apparatus of FIG. 1, according to an exemplary embodiment.
Figure 4:
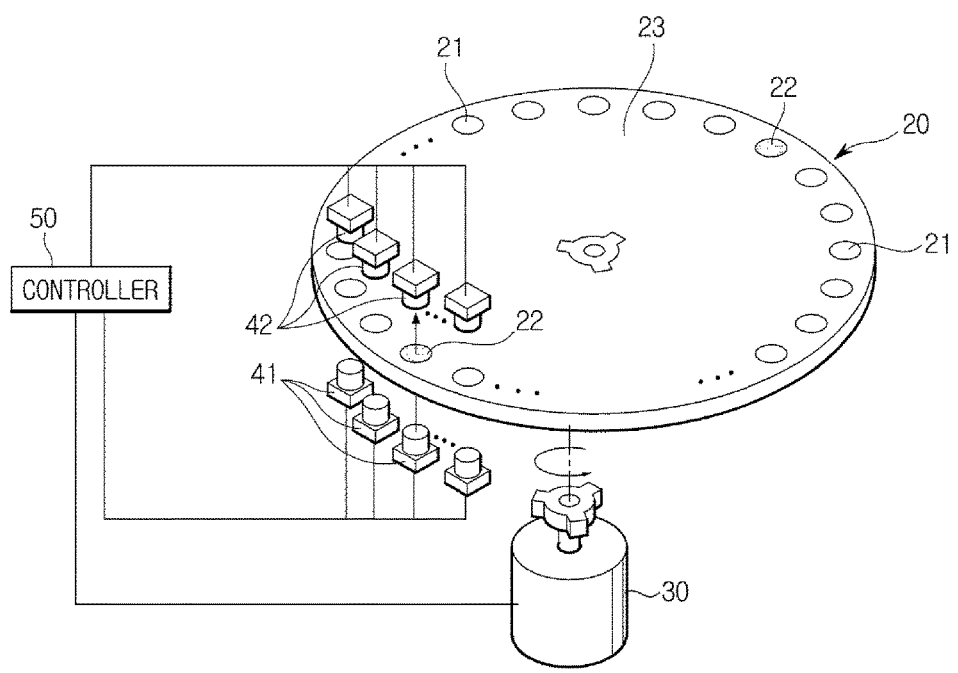
FIG. 4 is a perspective view showing the outer appearance of a reactor inserted into the test apparatus of FIG. 2, according to another exemplary embodiment.

FIG. 1 is a perspective view showing the outer appearance of a test apparatus, according to an exemplary embodiment; FIG. 2 is a perspective view showing the outer appearance of a test apparatus, according to another exemplary embodiment; FIG. 3 is a perspective view showing the outer appearance of a reactor inserted into the test apparatus of FIG. 1, according to an exemplary embodiment; and FIG. 4 is a perspective view showing the outer appearance of a reactor inserted into the test apparatus of FIG. 2, according to another exemplary embodiment.

A test apparatus 100 is a miniaturized and automated apparatus that can be used to test various kinds of samples, such as an environmental sample, a bio sample, a food sample, etc. In particular, when the test apparatus 100 is used for vitro diagnosis to test biological samples collected from the human body, the test apparatus 100 enables a user (for example, a patient, a doctor, a nurse, a medical technologist, etc.) to perform Point Of Care Testing (POCT) rapidly at any place, such as a home, an office, an outpatient clinic, a hospital room, an emergency room, an intensive care unit, etc., where a patient is located, as well as an examination room.

Meanwhile, a reactor into which a sample is injected to react with a reagent may include a cartridge type in which a sample or a reagent is moved by a capillary force, a disc type in which a sample or a reagent is moved by a centrifugal force, and a cuvette type in which measurement is performed without movement of a sample or a reagent. The structure or configuration of a test apparatus depends on the type of a reactor, and the exemplary embodiment shown in FIG. 1 shows a test apparatus into which a cartridge type reactor is inserted.

According to the exemplary embodiment of FIG. 1, the test apparatus 100 may include an installation part 103 which is space where a reactor 10 is installed. If a door 102 of the installation part 103 slides upward to open, the reactor 10 can be inserted into the test apparatus 100. More specifically, a part of the reactor 10 may be inserted into a predetermined insertion hole 104 formed in the installation part 103.

The part of the reactor 10 may be inserted into the inside of a main body 107, and the remaining part of the reactor 10 may be exposed to the outside of the test apparatus 100 and supported by a support 106. A pressing member 105 may press the reactor 10 to facilitate movement of a sample to a reaction zone.

If the reactor 10 is completely installed, the test apparatus 100 may close the door 102 in order to start a test.

The cartridge type reactor 10 inserted into the test apparatus 100 according to the exemplary embodiment of FIG. 1 may have an outer appearance as shown in FIG. 3.

Referring to FIG. 3, the reactor 10 according to an exemplary embodiment may include a housing 11, and a platform 12 in which a sample reacts with a reagent.

The housing 11 may support the platform 12, and allow a user to grip the reactor 10. The platform 12 may be coupled with the housing 11 in such a way so as to be attached on the lower surface of the housing 11 or inserted into a predetermined groove formed in the housing 11.

The housing 11 may be made of a chemically and biologically inert material that can be easily molded. For example, the housing 11 may be made of any of a plastic material, glass, mica, silica, a semiconductor wafer, and the like, wherein the plastic material may include acrylic (for example, polymethylmethacrylate (PMMA)), polysiloxane (for example, polydimethylsiloxane (PDMS)), polycarbonate (PC), polyethylene (for example, linear low density polyethylene (LLDPE), low-density polyethylene (LDPE), medium-density polyethylene (MDPE), and high-density polyethylene (HDPE)), polyvinyl alcohol, very low density polyethylene (VLDPE), polypropylene (PP), acrylonitrile-butadiene-styrene (ABS), cyclo-olefin copolymer (COC), and the like, although not limited to these.

The housing 11 may include an inlet hole 11a into which a sample is injected. The user may drop a sample to be test into the inlet hole 11a using a tool, such as a pipet or a spuit.

In the platform 12, a plurality of chambers 12a may be formed to accommodate a reagent. For example, the reagent may be applied on the inner surface of one of the chambers 12a and then dried. The sample injected into the inlet hole 11a may arrive at the chambers 12a via a channel (not shown) that connects the inlet hole 11a to the chambers 12a to react with the reagent accommodated in advance in the chambers 12a. As described above with reference to FIG. 1, a part of the reactor 10 may be inserted into the insertion hole 104 of the test apparatus 100. Since the sample reacts with the reagent in the chambers 12a, the platform 12 may be inserted into the insertion groove 104, and the pressing member 105 may press the inlet hole 11a to facilitate the flow of the sample.

Although not shown in the drawings, the platform 12 may be formed by bonding three plates. The three plates may include an upper plate, a lower plate, and a middle plate. On the upper plate and the lower plate, light-shielding ink may be printed to protect the sample moving to the chambers 12a from external light.

The upper plate and the lower plate may be formed with films, and the films used to form the upper plate and the lower plate may be ones selected from among a polyethylene film (for example, very low density polyethylene (VLDPE), linear low density polyethylene (LLDPE), low-density polyethylene (LDPE), medium-density polyethylene (MDPE), high-density polyethylene (HDPE), etc.), a polypropylene (PP) film, a polyvinyl chloride (PVC) film, a polyvinyl alcohol (PVA) film, a polystyrene (PS) film, and a polyethylene terephthalate (PET) film.

The middle plate may be formed with a porous sheet, such as cellulose, so that the porous sheet can function as a vent. Also, the porous sheet may be formed with a hydrophobic material or subject to hydrophobic treatment in order not to affect the movement of the sample.

As such, if the platform 12 has a three-layered structure, a hole forming the inlet hole 11a may be formed in the upper plate and the middle plate, and portions of the upper plate and the lower plate corresponding to the chambers 12a may be transparent. The reason why the portions of the upper plate and the lower plate corresponding to the chambers 12a are transparent is to facilitate measurements of optical characteristics due to reactions that occur in the chambers 12a.

In the middle plate, a thin channel may be formed, and a sample entered through the inlet hole 11a may be moved to the chambers 12a by the capillary force of the channel.

The chambers 12a may include a pigment chamber 12a' in which a thermochromic pigment is accommodated. The pigment chamber 12a' may be formed in the platform 12, similarly as the other chambers 12a. Also, a plurality of pigment chambers 12a' may be formed in the platform 12. Thermochromic pigments whose colors change in different temperature ranges may be accommodated in the form of slurry in the pigment chambers 12a'. The temperature of the reactor 10, that is, the temperature of the reagent or the sample accommodated in the chambers 12a, may be determined based on absorbance values of the thermochromic pigments.

The exemplary embodiment of FIG. 2 relates to a test apparatus 100 into which a disc type reactor 20 is inserted.

As shown in FIG. 2, the test apparatus 100 may include a tray 102 on which the disc type reactor 20 can be rested. The reactor 20 may be inserted into the inside of the main body 107 of the test apparatus 100, together with the tray 102. If the reactor 20 is inserted, the test apparatus 100 may rotate the reactor 20 and perform a test, according to the kind of the reactor 20, the kind of a sample, and/or a predetermined sequence determined by a test process.

Referring to FIG. 4, the disc type reactor 20 may be configured with a rotatable platform 23 and a plurality of structures formed in the platform 23. The structures may include a plurality of chambers configured to receive a sample or a reagent, and a channel configured to connect the chambers to each other. The structures may be formed in the inside of the reactor 20. In the current exemplary embodiment, the reactor 20 may be made of a transparent material so that the structures formed in the inside of the reactor 20 can be seen from above.

The platform 23 may be made of a material which can be easily molded and whose surface is biologically inert. For example, the platform 23 may be made of any of a plastic material, glass, mica, silica, a silicon wafer, and the like, wherein the plastic material may include acrylic (PMMA), polydimethylsiloxane (PDMS), polycarbonate (PC), polypropylene (PP), polyvinyl alcohol (PVA), polyethylene (PE), and the like.

As shown in FIG. 4, the disc type reactor 20 may accommodate a thermochromic pigment, and may be in the shape of a disc that can be rotated by a centrifugal force. That is, the disc type reactor 20 may be rotated by rotation of a rotation driver 30.

The disc type reactor 20 may include the plurality of chambers, and the chambers may include a reaction chamber 21 in which a reagent is accommodated, and a pigment chamber 22 in which a thermochromic pigment is accommodated. The pigment chamber 22 may be formed in the platform 23, like the reaction chamber 21. There may be provided a plurality of pigment chambers 22.

Thermochromic pigments whose colors change in different temperature ranges may be accommodated in the form of slurry in the pigment chambers 22. The thermochromic pigments accommodated in the pigment chambers 22 may be compounded with different colors and concentrations according to the purposes of tests and the kinds of samples.

According to an exemplary embodiment, a thermochromic pigment, which is in the form of a powder or a slurry, may be coated on a film, and then the film may be fixed and attached on the disc type reactor 20. Also, a thermochromic pigment may be added in a plastic resin being a base material of the disc type reactor 20, and then the plastic resin may be fabricated in the form of a master batch. Also, a thermochromic pigment may be formed in the form of a lateral flow strip on the reactor 20. As described above, the thermochromic pigment may be accommodated in the pigment chamber 22, or provided in the reactor 20 in various forms.

The above-described forms in which the thermochromic pigment is provided in the reactor 20 may be applied in the same way to the cartridge type reactor 10 as described above with reference to FIG. 3.

Although not shown in FIG. 4, in the center portion of the disc type reactor 20, a sample chamber configured to accommodate a sample such as blood, a dilution chamber configured to accommodate another reagent such as diluent that can be mixed with a sample, a plurality of channels configured to connect the chambers to each other, and a valve configured to control the flow of fluid through the plurality of channels may be further provided.

If the disc type reactor 20 rotates at high speed, a sample contained in the sample chamber may flow to the outer portion of the reactor 20 along the channels by a centrifugal force so as to be mixed with other reagents and then enter the reaction chambers 21.

The disc type reactor 20 may be not necessarily in the shape of a disc. For example, the disc type reactor 20 may be in the shape of a fan that can be rested on a rotatable frame to rotate, as well as in the shape of a complete disc that can rotate by itself. The disc type reactor 20 may be made of a plastic material, such as acrylic (PMMA), PDMS, PC, and the like, which can be easily molded and whose surface is biologically inert. However, the disc type reactor 20 may be made of any other material having chemical, biological stability, optical transparency, and machinability.

The rotation driver 30 may rotate the disc type reactor 20 at a high speed to provide a centrifugal force so that a sample enters the reaction chambers 21. Also, the reactor 20 may rotate to enable the reaction chambers 21 and the pigment chambers 22 to face a plurality of light emitters 41 and a plurality of light receiver 42.

The light emitters (for example, LEDs) 41 may be arranged below the reactor 20 including the reaction chambers 21 and the pigment chambers 22, and the light receivers 42 may be arranged above the reactor 20.

The light emitters 41 may be arranged at regular intervals to face the reaction chambers 21 and the pigment chambers 22 of the reactor 20, and the light receivers 42 may also be arranged at regular intervals to face the reaction chambers 21 and the pigment chambers 22 of the reactor 20. The light emitters 41 may be disposed to correspond to the light receivers 42 so that a plurality of different wavelengths can be measured with respect to each reaction chamber 21 while the reactor 20 rotates.

In particular, the plurality of light emitters 41 can irradiate light of different wavelengths of 200 nm to 900 nm with respect to the thermochromic pigments accommodated in the pigment chambers 22, onto the pigment chambers 22 in which the thermochromic pigments are accommodated, so that an experimenter can select a wavelength for measurement according to a purpose. While an absorbance value is measured using one of the light emitters 41, the remaining light emitters 41 may be turned off so that no error is generated in measuring the absorbance value.

One of the light emitters 41 may irradiate light of different wavelengths, or the respective light emitters 41 may irradiate light of different wavelengths.

If the plurality of light emitters 41 irradiate light of different wavelengths onto the pigment chambers 22 in which the thermochromic pigments are accommodated, the light receivers 42 may receive a plurality of light that propagates through the pigment chambers 22, and a controller 50 may measure the transmittance of light, that is, absorbance values. A temperature of the reactor 20 in which the thermochromic pigments are accommodated may be measured based on the absorbance values measured by the plurality of light receivers 42.

The controller 50 may control operations of the rotation driver 30, the light emitters 41, and the light receivers 42. More specifically, the controller 50 may detect a rotation phase of the rotation driver 210 to control the light emitters 41 to irradiate light based on the detected rotation phase, and may measure absorbance values of the thermochromic pigments accommodated in the pigment chambers 22.

The controller 50 may measure absorbance values of the thermochromic pigments to thus measure the temperature of the reactor 20 in which the pigment chambers 22 containing the thermochromic pigments are disposed. The controller 50 may determine whether the measured temperature of the reactor 20 is a predetermined temperature (for example, 37° C.) suitable for immunoassay. If the controller 50 determines that the measured temperature of the reactor 20 is lower than the predetermined temperature suitable for immunoassay, the controller 50 may determine that temperature of a sample accommodated in the reactor 20 is also lower than the predetermined temperature. Then, the controller 50 may control heating of the reactor 20 based on the result of the determination, and when the temperature of the reactor 20 reaches the predetermined temperature suitable for immunoassay, the controller 50 may start a test.

The above descriptions may be applied in the same way to the cartridge type reactor 10 described above with reference to FIG. 3.

Figure 5:
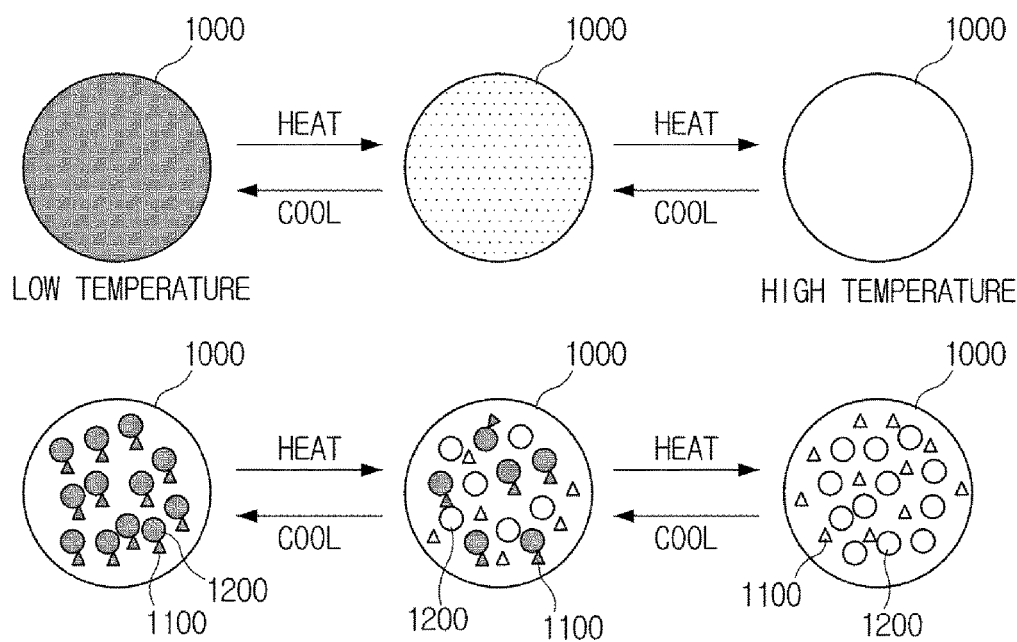
FIG. 5 is a view for describing operation characteristics of a thermochromic pigment, according to an exemplary embodiment.
Figure 6:
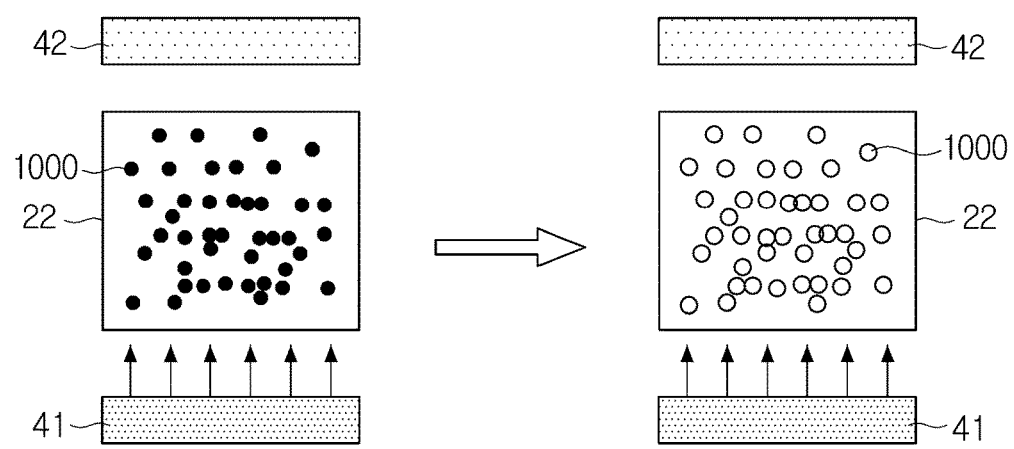
FIG. 6 is a view for describing an optical measurement principle of a thermochromic pigment, according to an exemplary embodiment.

FIG. 5 is a view for describing operation characteristics of a thermochromic pigment, according to an exemplary embodiment; and FIG. 6 is a view for describing an optical measurement principle of a thermochromic pigment, according to an exemplary embodiment.

Referring to FIG. 5, a thermochromic pigment 1000, which is a reversible, thermo-photosensitive material whose color changes according to temperature, may be a microcapsule composed of an electron donor 1100 which emits electrons and an electron acceptor 1200 which receives electrons.

The thermochromic pigment 1000 may have a color on the crystal which is based on an interaction of the electron donor 1100 and the electron acceptor 1200. If temperature rises (high temperature), the electron donor 1100 and the electron acceptor 1200 may be separated from each other so as to look transparent (there is no color), and if temperature falls, the electron acceptor 1200 may be again combined with the electron donor 110 so as to have a color.

Also, at low temperature, the thermochromic pigment 1000 may have a high absorbance value to absorb a large amount of light, and at high temperature, the thermochromic pigment 1000 may have a low absorbance value to absorb a small amount of light.

The thermochromic pigment 1000 may have base colors of red, rose red, orange, yellow, sky blue, fast blue, dark blue, violet, green, and black, and may mix some of the base colors to have other colors.

The thermochromic pigment 1000 may be made of any of spiropyrans, ethylenic compounds (for example, dixanthylene, bianthrone, and xanthylideneanthrone), disulfide (for example, diphenyldisulfide and β-dinaphthyldi-sulfide), polyamide-diacetylene, or the like. The thermochromic pigment 1000 may be in the form of a powder, a slurry, a master batch, or a film. A resin to which the master batch can be applied may include any of PE, PP, PS, PMMA, COC, AS, PVC, and the like.

Referring to FIG. 6, the light emitter 41 and the light receiver 42 may be respectively disposed below and above the pigment chamber 22 in which the thermochromic pigment 1000 is accommodated, so that a degree of color change of the thermochromic pigment 1000 can be measured by using optical transmittance.

If the light emitter 41 irradiates light onto the pigment chamber 22 in which the thermochromic pigment 1000 is accommodated, the light may propagate through the pigment chamber 22 and then be received by the light receiver 42, and the light may be transferred to the controller 50. The controller 50 may measure transmittance (that is, an absorbance value) of the light that has propagated through the pigment chamber 22. Since the absorbance value measured by the controller 50 depends on a degree of color change of the thermochromic pigment 1000, the controller 50 can measure a temperature of the thermochromic pigment 1000 and simultaneously measure a temperature of the reactor 200 accommodating the thermochromic pigment 1000, through the measurement of the absorbance value.

Herein, a temperature range in which the color of the thermochromic pigment 1000 changes may be selected from a temperature range of −15° C. to 220° C.

The light emitters 41 may irradiate light of a wavelength range of 200 nm to 900 nm that can be optically measured, according to the color of the thermochromic pigment 1000, toward the pigment chamber 22 in which the thermochromic pigment 1000 is accommodated. Accordingly, the concentration of the thermochromic pigment 1000 may be adjusted according to a wavelength range which can be optically measured.

An absorbance value measured at a wavelength that can be optically measured according to the color and concentration of the thermochromic pigment 1000 may be selectively used by the experimenter according to the purpose of the test and the kind of the sample.

Figure 7:
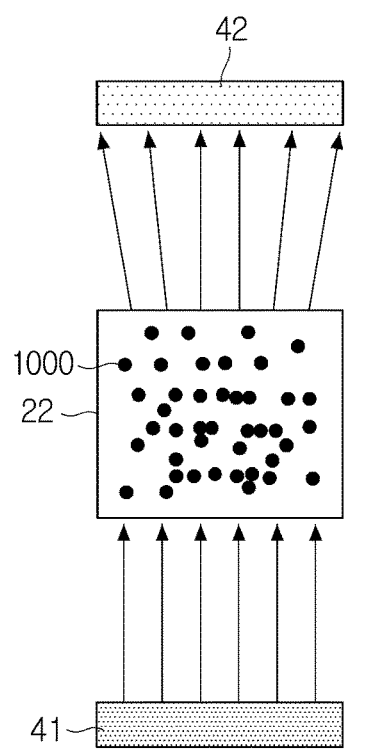
FIG. 7 is a view for describing structural deviation between test apparatuses that measure absorbance values of a thermochromic pigment.
Figure 7:
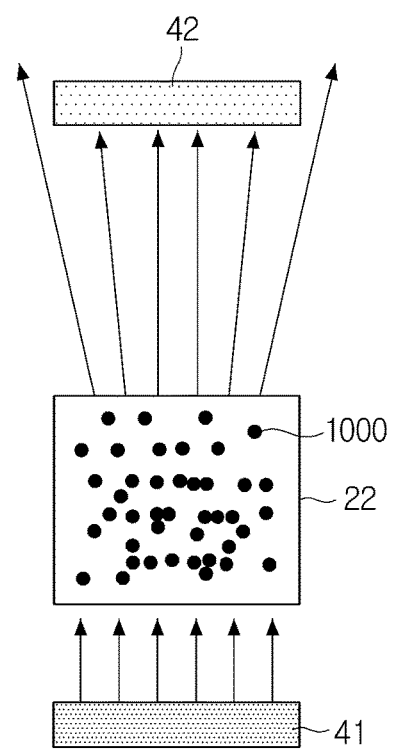
Figure 8:
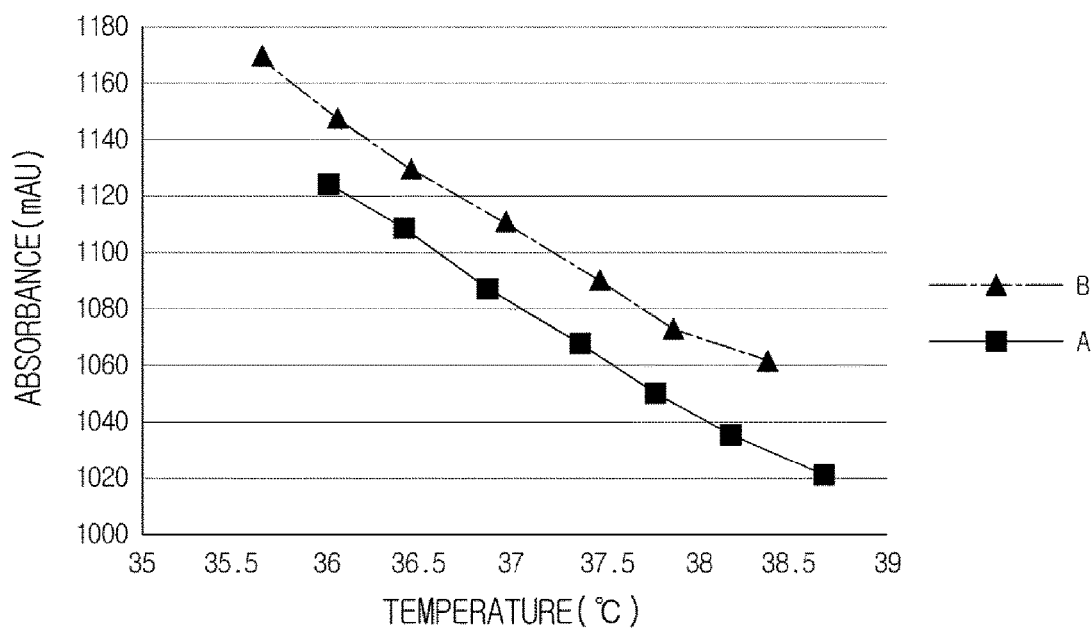
FIG. 8 is a graph showing different temperature values measured by the test apparatuses due to the structural deviation shown in FIG. 7.

FIG. 7 is a view for describing a structural deviation between test apparatuses that measure absorbance values of a thermochromic pigment, and FIG. 8 is a graph showing different temperature values measured by the test apparatuses due to the structural deviation shown in FIG. 7.

Referring to FIG. 7, there may be various kinds of test apparatuses. For convenience of description, the test apparatuses will be referred to as a test apparatus A and a test apparatus B. Although the test apparatuses are used for the same purpose of blood analysis, the test apparatuses may have mechanical deviation depending on the positions or structural characteristics of components included in the test apparatuses, such as the light emitters 41, the light receivers 42, etc.

Also, as described above, the light emitter 41 may irradiate light onto the pigment chamber 22 of the reactor 20 in which the thermochromic pigment 1000 is accommodated, and the light may propagate through the thermochromic pigment 1000 and then received by the light receiver 42. The light that propagates through the thermochromic pigment 1000 may be absorbed or scattered. Accordingly, an absorbance value may vary depending on the distance between the light receiver 42 and the pigment chamber 22 accommodating the thermochromic pigment 1000, and temperature of the reactor 20 measured based on the absorbance value may also change accordingly.

As shown in FIG. 7, in the test apparatus A, since the pigment chamber 22 is located relatively closer to the light receiver 42 than in the test apparatus B, light that propagates through the pigment chamber 22 may be less scattered so that a major portion of the light can be incident to the light receiver 42. Accordingly, the light receiver 42 may receive a relatively large amount of the light that has propagated through the thermochromic pigment 1000, so that the controller 50 may measure a relatively low absorbance value in the test apparatus A.

In contrast, in the test apparatus B, since the pigment chamber 22 is located relatively more distant from the light receiver 42 than in the test apparatus A, a part of light that propagate through the pigment chambers 22 may be scattered so as not to be incident to the light receiver 42. Accordingly, the light receiver 42 may receive a relatively small amount of the light that propagates through the thermochromic pigment 1000, so that the controller 50 may measure a relatively high absorbance value in the test apparatus B.

As a result, when the test apparatus A and the test apparatus B measure absorbance values using the same thermochromic pigment 1000, the test apparatus A and the test apparatus B may measure different absorbance values due to a structural deviation which corresponds to a difference in distance between the pigment chamber 22 and the light receiver 42. Accordingly, the test apparatus A and the test apparatus B may also measure a temperature of the reactor 20, as different values, based on the different absorbance values. In other words, the temperature of the reactor 20 measured using the same thermochromic pigment 1000 may vary according to the test apparatus 100.

FIG. 8 is a graph showing a correlation between absorbance and temperature with respect to the test apparatus A and the test apparatus B. As described above with reference to FIG. 7, when different test apparatuses 100 measure the temperature of the reactor 20 using the same thermochromic pigment 1000, the test apparatuses 100 may measure different absorbance values according to a difference between them.

In particular, whether the temperature of the reactor 20 corresponds to temperature suitable for a test may be determined based on data about a correlation between absorbance and temperature stored in a memory 60. For example, when an absorbance value is measured as 1100 mAU corresponding to a reference absorbance value, temperature of the reactor 20 may be decided as 36.5° C. corresponding to 1100 mAU. However, if an absorbance value is measured as 1130 mAU that is higher than the reference absorbance value, due to the structural deviation of the test apparatus 100 as described above with reference to FIG. 7, the controller 50 may determine the temperature of the reactor 20 as 36° C. corresponding to 1130 mAU, based on the data stored in the memory 60.

That is, when another test apparatus 100 is used, the test apparatus 100 may measure a different absorbance value due to the structural deviation, and compare the measured absorbance value to pre-stored data in order to determine the temperature of the reactor 20 as a different value.

Referring to FIG. 8, data about a correlation between absorbance and temperature which is stored in the memory 60 is assumed to be identical to data about a graph of the test apparatus A. In this case, if the test apparatus A measures an absorbance value of 1100 mAU, the test apparatus A may decide temperature of the reactor 20 as 36.5° C. corresponding to 1100 mAU.

Meanwhile, if the test apparatus B measures a higher absorbance value of 1130 mAU than the test apparatus A, the test apparatus B may decide temperature of the reactor 20 as 36° C. corresponding to 1130 mAU. Since the test apparatus A and the test apparatus B measure different absorbance values, the test apparatus A and the test apparatus B may also determine the temperature of the reactor 20 as different values, based on the different absorbance values.

The test apparatus 100 and a control method thereof according to exemplary embodiments can provide an effect of reducing an error according to the test apparatus 100. The test apparatus 100 and the control method thereof will be described below in more detail with reference to the accompanying drawings.

Figure 9:
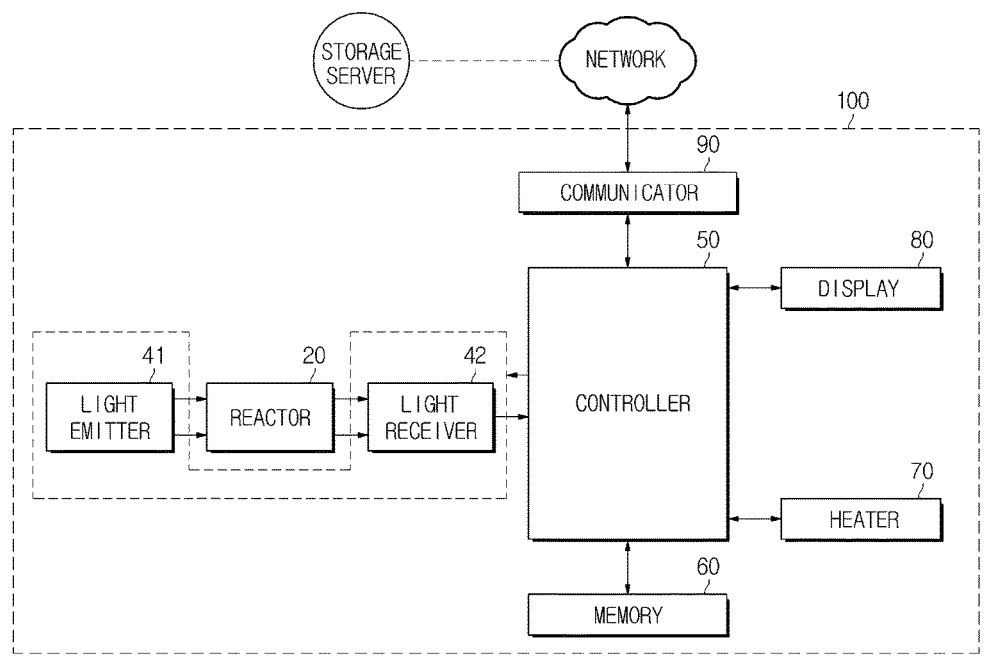
FIG. 9 is a control block diagram showing a configuration of the test apparatus 100, according to an exemplary embodiment.

FIG. 9 is a control block diagram showing a configuration of the test apparatus 100, according to an exemplary embodiment.

A reactor that is inserted into the test apparatus 100 may be the cartridge type reactor 10 described above with reference to FIG. 3 or the disc type reactor 20 described above with reference to FIG. 4. In the following description, for convenience of description, the reactor is assumed to be the disc type reactor 20.

Referring to FIG. 9, the test apparatus 100 may include the light emitter 41 configured to irradiate light onto the reaction chamber 21 or the pigment chamber 22 of the reactor 20, the light receiver 42 configured to receive light that propagates through the reactor 20, the controller 50 configured to control overall operations of the test apparatus 100, the memory 60 configured to store data related to the control of the test apparatus 100, a heater 70 configured to heat the reactor 20 to adjust the temperature of the reactor 20, a display 80 configured to provide a user with information related to the operations and control of the test apparatus 100, and a communicator 90 configured to enable the test apparatus 100 to transmit/receive data to/from an external server or to store data related to the control of the test apparatus 100 in the external server.

There may be provided a plurality of light emitters 41 and a plurality of light receivers 42, and the light emitters 41 and the light receivers 42 may be arranged at regular spatial intervals to face the reaction chamber 21 and the pigment chamber 22 of the reactor 20, as described above with reference to FIG. 4.

The light emitter 41 may be implemented as a point light source or a surface light source to irradiate light onto the reactor 20. For example, the light emitter 41 may be a back light unit. Alternatively, the light emitter 41 may be a light source that be turned on/off according to predetermined frequency. For example, the light emitter 41 may be a semiconductor light emitting device, such as a Light Emitting Diode (LED) or a Laser Diode (LD), or a gas discharge lamp, such as a halogen lamp or a Xenon lamp.

The light receiver 42 may detect light irradiated from the light emitter 41 and then transmitted through or reflected against a sample or a thermochromic pigment accommodated in the chambers 21 and 22 of the reactor 20, and generate an electrical signal according to the intensity of the light for measuring an absorbance value. The light receiver 42 may be a depletion layer photodiode, an avalanche photodiode, or a photomultiplier tube. Also, the light receiver 42 may be implemented as a Complementary Metal-Oxide Semiconductor (CMOS) image sensor or a Charged Coupled Device (CCD) image sensor.

The light emitter 41 and the light receiver 42 may be disposed to face each other with the reactor 20 in between, or may be disposed above or below the reactor 20. Also, power for moving the light emitter 41 and the light receiver 42 may be provided by a motor (not shown) of the test apparatus 100. The controller 50 may control driving of the motor to control movements of the light emitter 41 and the light receiver 42.

The intensity or wavelength of light irradiated from the light emitter 41 may be adjusted according to a command of the controller 50. The light receiver 42 may transmit the electrical signal generated by detecting light to the controller 50. The light emitter 41 and the light receiver 42 may further include an A/D converter configured to convert the result of detection by the light receiver 42 into a digital signal, and output the digital signal to the controller 50.

The plurality of light emitters 41 may irradiate light of different wavelengths of 200 nm to 900 nm with respect to the thermochromic pigment accommodated in the pigment chambers 22, onto the pigment chambers 22 in which the thermochromic pigment is accommodated. An experimenter may select a wavelength for measurement according to a purpose.

According to an exemplary embodiment, the light emitter 41 may irradiate light of two wavelengths, that is, light of a first wavelength and light of a second wavelength. The light of the first wavelength and the light of the second wavelength may be respectively irradiated from two light emitters 41, or may be sequentially irradiated with a time difference from a single light emitter 41. However, the light irradiated from the light emitter 41 is not limited to light having two wavelengths, and may be light based on three or more wavelengths.

The second wavelength may be preferably longer than the first wavelength. That is, the first wavelength and the second wavelength may be different wavelengths. For example, the first wavelength may be a wavelength of 450 nm to 570 nm, and the second wavelength may be a wavelength of 810 nm. However, the first and second wavelengths are not limited to these lengths, and may have any other lengths.

Also, the first wavelength may be a wavelength at which an absorbance value changes greatly according to temperature, and the second wavelength may be a wavelength at which an absorbance value changes slightly according to temperature, which will be described below with reference to FIG. 10. That is, in the test apparatus and the control method thereof according to the exemplary embodiments, light having two wavelengths may be irradiated, and a temperature of the reactor 20 may be determined based on an absorbance difference according to the two wavelengths. Since the temperature of the reactor 20 can be determined more accurately at the greater absorbance difference, the first and second wavelengths can be selected as described above.

The controller 50 may control the light emitter 41 to irradiate light of the first wavelength and light of the second wavelength onto the thermochromic pigment accommodated in the reactor 20, and control the light receiver 42 to receive light that has propagated through the thermochromic pigment and transmit an electrical signal converted from the received light to the controller 50.

Before light is irradiated onto the thermochromic pigment accommodated in the reactor 20 to measure an absorbance value, the controller 50 may raise the temperature of the thermochromic pigment and then lower the temperature of the thermochromic pigment.

Since the thermochromic pigment accommodated in the reactor 20 may be stored at low temperature, and the thermochromic pigment stored at low temperature for a relatively long time may have a correspondingly low thermo-sensitivity, the controller 50 may activate the thermo-sensitivity of the thermochromic pigment, before measuring temperature of the thermochromic pigment by measuring an absorbance value.

Accordingly, before a command for measuring temperature of the reactor 20 is received from a user, or before light is irradiated onto the thermochromic pigment accommodated in the reactor 20 based on a predetermined control program, the controller 50 may control the heater 70 to increase the temperature of the reactor 20 one time, and then stop operating the heater 70 to decrease the temperature of the reactor 20 one time. In this way, by controlling the temperature of the reactor 20, the accuracy of thermo-sensitivity of the thermochromic pigment accommodated in the reactor 20 can be improved.

The controller 50 may measure an absorbance value (hereinafter, referred to as a first absorbance value) of the thermochromic pigment in correspondence to the light of the first wavelength that has propagated through the pigment chambers 22, and also, the controller 50 may measure an absorbance value (hereinafter, referred to as a second absorbance value) of the thermochromic pigment in correspondence to the light of the second wavelength that has propagated through the pigment chambers 22, based on electrical signals received from the light receiver 42. That is, the controller 50 may measure absorbance values based on electrical signals with respect to light irradiated from the light emitter 41, absorbed in the thermochromic pigment, and then received by the light receiver 42.

Also, the controller 50 may calculate a difference between the first absorbance value and the second absorbance value measured by the above-described method, and determine the temperature of the reactor 20 in correspondence to the calculated difference between the first absorbance value and the second absorbance value. Since the memory 60 stores data about temperature of the reactor 20 corresponding to the difference between the first absorbance value and the second absorbance value, in addition to data about temperature of the reactor 20 corresponding to an absorbance value of the thermochromic pigment, the controller 50 may compare the difference between the first absorbance value and the second absorbance value to data stored in the memory 60 in order to determine a temperature of the reactor 20 based on the difference between the first absorbance value and the second absorbance value.

After the controller 50 determines the temperature of the reactor 50, the controller 50 may compare the determined temperature to data stored in advance in the memory 60 in order to determine whether the temperature of the reactor 20 corresponds to a predetermined temperature suitable for a test. If the controller 50 determines that the temperature of the reactor 20 is lower than the predetermined temperature, the controller 50 may control the heater 70 to heat the reactor 20 until the temperature of the reactor reaches the predetermined temperature.

That is, the memory 60 may store data about appropriate temperature of the reactor 20 so that the test apparatus 100 can test medium to be tested, and the data about the appropriate temperature may be a specific temperature value or data about a predetermined temperature range.

The controller 50 may determine the temperature of the reactor 20, and compare the temperature of the reactor 20 to the data about the appropriate temperature of the reactor 20. If the controller 50 determines that the determined temperature is not identical to the appropriate temperature or that the determined temperature is not within an appropriate temperature range, the controller 70 may control the heater 70 so that the temperature of the reactor 20 reaches the appropriate temperature or belongs to the appropriate temperature range.

Also, if the reactor 20 includes identification information 200 containing information about temperature, the controller 50 may identify the identification information attached on the reactor 20 to compare data about appropriate temperature of the reactor 20 for performing a predetermined test to the temperature of the reactor 20 determined according to the above-described method, which will be described below. If the controller 50 determines that the determined temperature of the reactor 20 does not correspond to the appropriate temperature of the reactor 20 for performing the predetermined test, the controller 50 may transmit a control signal to the display unit 80, and the display unit 80 may display information indicating that the current temperature of the reactor 20 is not an appropriate temperature for performing a test in order to inform the user.

The controller 50 may include a main processor, a graphic processor, and memory.

The memory 60 may store control programs or control data for controlling operation of the test apparatus 100, control command data output from the controller 50, or image data output from the graphic processor.

Also, the memory 60 may store information related to control operations, according to an exemplary embodiment. More specifically, the memory 60 may store data about wavelengths of light that is irradiated from the light emitter 41 so that the controller 50 can select light to be irradiated and control the light emitter 40 to irradiate the selected light onto the reactor 20.

The memory 60 may store data of an absorbance value for light that propagates through the thermochromic pigment accommodated in the pigment chambers 22 of the reactor 20. For example, the memory 60 may store information about the first absorbance value of the thermochromic pigment corresponding to the light of the first wavelength that propagates through the pigment chambers 22. Also, the memory 60 may store information about the second absorbance value of the thermochromic pigment corresponding to the light of the second wavelength that propagates through the pigment chambers 22.

Also, the memory 60 may store data about the temperature of the reactor 20 corresponding to the difference between the first absorbance value and the second absorbance value, and provide the data to the controller 50.

Also, the memory 60 may store data about an appropriate temperature of a sample and an appropriate temperature of the reactor 20, suitable for the test apparatus 100 to perform various kinds of tests, such as a blood test, blood analysis, etc., and also store data about a heating time of the heater 70 for heating the reactor 20 until the temperature of the reactor 20 reaches a predetermined temperature.

The memory 60 may be at least one type of storage medium from among a flash memory type, a hard disc type, a multimedia card micro type, card type memory (for example, a Secure Digital (SD) card or an eXtreme Digital (XD) card), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, a magnetic disc, and an optical disc.

The heater 70 may determine whether the temperature of the reactor 20 measured by the controller 50 according to the absorbance value of the thermochromic pigment corresponds to a predetermined temperature suitable for immunoassay or a clinical chemical test. If the heater 70 determines that the temperature of the reactor 20 is lower than the predetermined temperature, the heater 70 may heat the reactor 20 under the control of the controller 50 until the temperature of the reactor 20 reaches the predetermined temperature suitable for the test. The heater 70 may be disposed above and below the tray on which the disc type reactor 20 is rested, so that the heater 70 can heat the reactor 20 at its both sides.

The display 80 may display the result of the test performed by the test apparatus 100. Since the reactor 20 can include a plurality of chambers 21 and 22 as described above, a plurality of test items may be detected from the reactor 20, and if a plurality of test items are detected, the display 80 may display the detection results for the plurality of test items. Also, the display 80 may provide the user with various information related to the test apparatus 100, and may display a screen to provide an absorbance value for light that propagates through the thermochromic pigment and information related to temperature of the reactor 20.

The display 80 may be implemented as a Liquid Crystal Display (LCD), Light Emitting Diodes (LED), Organic Light Emitting Diodes (OLED), Active Matrix Organic Light Emitting Diodes (AMOLED), a flexible display, or a 3D display. Also, the display 80 may include a touch screen configured to receive touch inputs from the user.

The communicator 90 may enable the test apparatus 100 to communicate with an external device. More specifically, the communicator 90 may transmit data acquired by or stored in the test apparatus 100 to an external device so that content displayed on the display 80 can be displayed on the external device. Also, data related to the operations and control of the test apparatus 100, which can be stored in the memory 60, may be stored in an external storage server via the communicator 90.

The communicator 90 may include at least one communication module from among a Bluetooth communication module configured to perform one-to-one communication with a single external device or one-to-many communication with several external devices, a Wireless Fidelity (WiFi) communication module configured to connect to a Local Area Network (LAN) through an Access Point (AP), and a short-range communication module, such as a Zigbee communication module, configured to form a short-range communication network between the test apparatus 100 and an external device. However, the communication module included in the communicator 90 is not limited to the Bluetooth communication module, the WiFi communication module, and the short-range communication module. That is, the communication module may include any other communication modules that can perform communications according to various communication standards.

Figure 10:
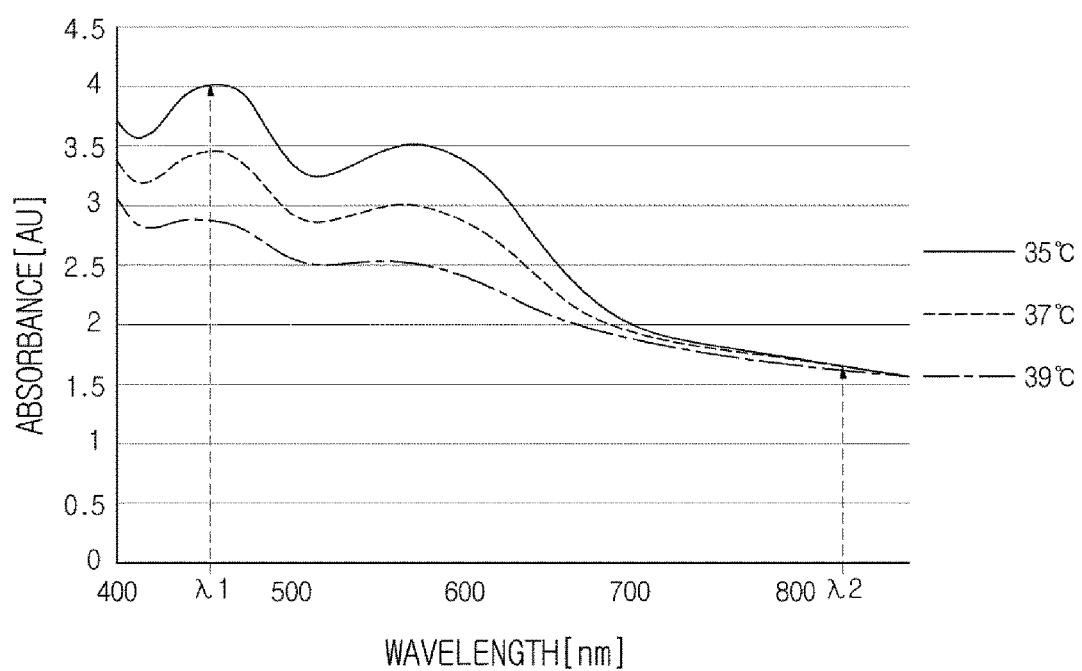
FIG. 10 is a graph showing absorbance values of a thermochromic pigment with respect to wavelengths and temperature.

FIG. 10 is a graph showing absorbance values of a thermochromic pigment with respect to wavelengths and temperature.

In FIG. 10, in the case in which the test apparatus A is used, absorbance values representing degrees of light absorption according to wavelengths for the temperature of a thermochromic pigment are shown as a graph. Since the thermochromic pigment is accommodated in the reactor 20, the graph shown in FIG. 10 can be interpreted as a temperature graph of the reactor 20.

As shown in FIG. 10, when the temperature of a thermochromic pigment accommodated in the reactor 20 is 35° C., 37° C., and 39° C., an absorbance value AU corresponding to a wavelength irradiated from the light emitter 41 may be determined based on the temperature graph. That is, as described above, the light emitter 41 may irradiate light of a first wavelength $\lambda 1$ and light of a second wavelength $\lambda 2$, wherein the light of the first wavelength $\lambda 1$ can acquire an absorbance value changing greatly according to the temperature of the reactor 20, and the light of the second wavelength $\lambda 2$ can acquire an absorbance value changing slightly according to the temperature of the reactor 20, as seen from FIG. 10.

When the light of the first wavelength $\lambda 1$ is irradiated, an absorbance value of the thermochromic pigment of the reactor 20 may correspond to 4 AU at 35° C., 3.4 AU at 37° C., and 2.7 AU at 39° C. Also, when the light of the second wavelength $\lambda 2$ is irradiated, an absorbance value of the thermochromic pigment of the reactor 20 may correspond to 1.5 AU at 35° C., 37° C., and 39° C. That is, as described above, an absorbance value for the light of the first wavelength $\lambda 1$ may change greatly depending on the temperature of the reactor 20, whereas an absorbance value for the light of the second wavelength $\lambda 2$ may change slightly depending on the temperature of the reactor 20.

Figure 11:
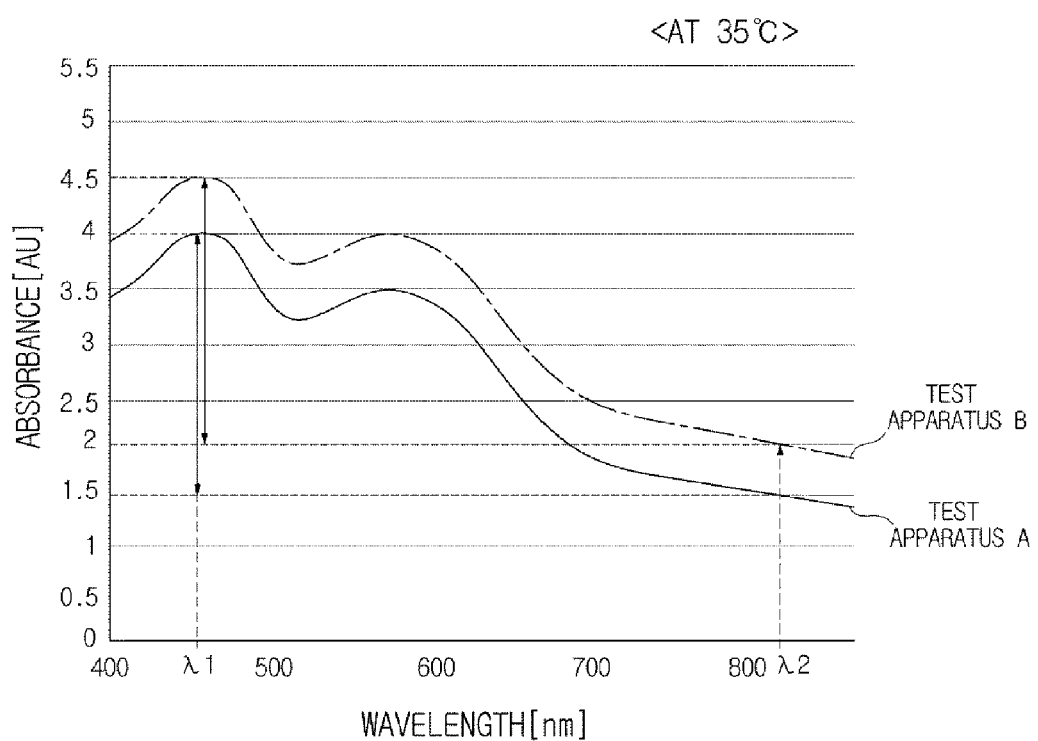
FIG. 11 is a graph showing absorbance values of a thermochromic pigment with respect to wavelengths and temperature for each of test apparatuses, according to an exemplary embodiment.
Figure 12:
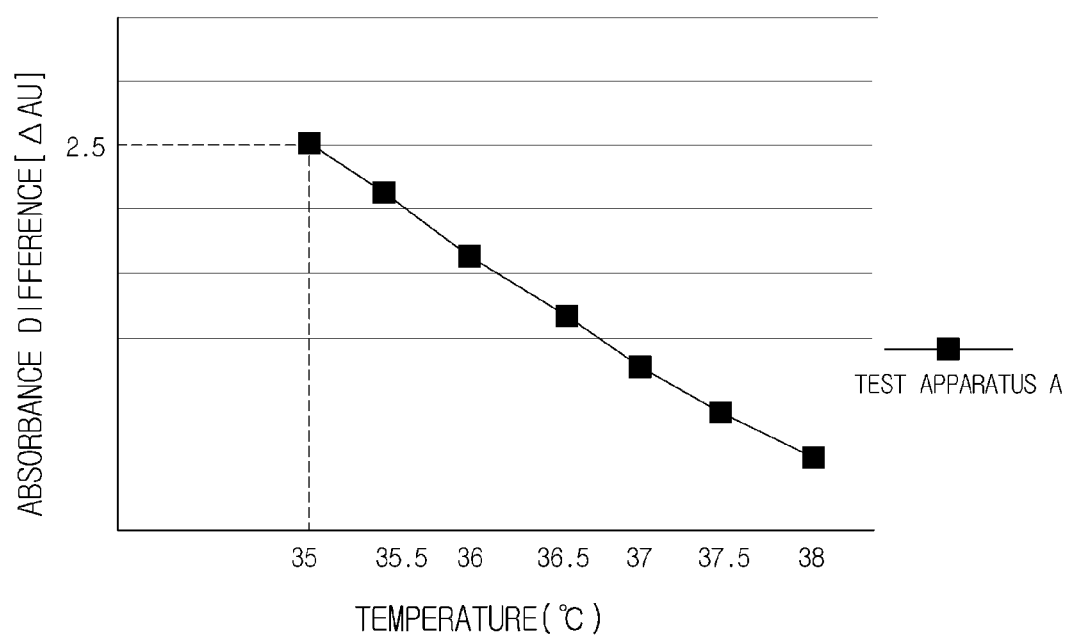
FIG. 12 is a graph for describing an operation of determining a temperature of a reactor in correspondence to an absorbance difference measured when a test apparatus A according to an exemplary embodiment irradiates light of a first wavelength and light of a second wavelength.
Figure 13:
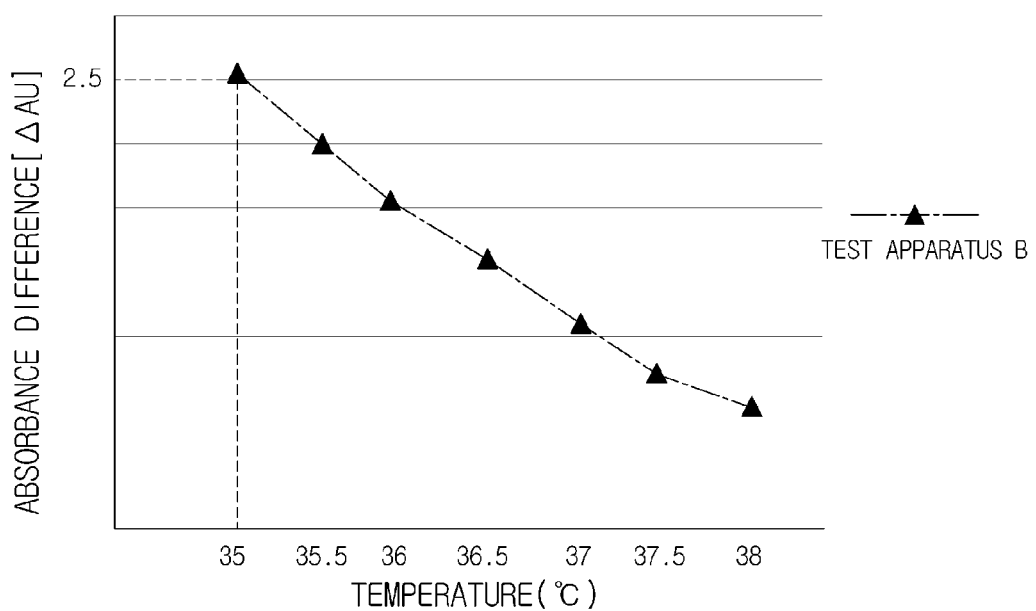
FIG. 13 is a graph for describing operation of determining a temperature of a reactor in correspondence to an absorbance difference measured when a test apparatus B according to an exemplary embodiment irradiates light of a first wavelength and light of a second wavelength.

FIG. 11 is a graph showing absorbance values of a thermochromic pigment with respect to wavelengths and temperature for each of test apparatuses, according to an exemplary embodiment; FIG. 12 is a graph for describing an operation of determining a temperature of a reactor in correspondence to an absorbance difference measured when a test apparatus A according to an exemplary embodiment irradiates light of a first wavelength and light of a second wavelength; and FIG. 13 is a graph for describing an operation of determining a temperature of a reactor in correspondence to an absorbance difference measured when a test apparatus B according to an exemplary embodiment irradiates light of a first wavelength and light of a second wavelength.

As shown in FIG. 11, the test apparatus A and the test apparatus B measure different absorbance values under the temperature condition of 35° C. described above with reference to FIG. 10. As described above with reference to FIGS. 7 and 8, when the test apparatus A and the test apparatus B measure absorbance values of a thermochromic pigment at the same temperature, the test apparatus A and the test apparatus B should measure the same absorbance value of the thermochromic pigment at the same temperature. However, due to the structural deviation between the test apparatuses A and B, the test apparatus A and the test apparatus B may measure the different absorbance values In this aspect, referring to FIG. 11, if both the temperature of the reactor 20 included in the test apparatus A and the temperature of the reactor 20 included in the test apparatus B are 35° C., the temperature of the thermochromic pigment accommodated in the reactor 20 may also be 35° C., and the test apparatus A and the test apparatus B should measure the same absorbance value when the thermochromic pigment absorbs the same wavelength of light. However, due to the above-described structural deviation, the test apparatus B may measure a higher absorbance value than the test apparatus A.

In particular, when light of a first wavelength $\lambda 1$ is absorbed, an absorbance value of the thermochromic pigment of the test apparatus A may be measured as 4 AU, and an absorbance value of the thermochromic pigment of the test apparatus B may be measured as 4.5 AU. Also, when light of a second wavelength $\lambda 2$ is absorbed, an absorbance value of the thermochromic pigment of the test apparatus A may be measured as 1.5 AU, and an absorbance value of the thermochromic pigment of the test apparatus B may be measured as 2 AU.

The test apparatus and the control method thereof according to the exemplary embodiments can determine a temperature of the reactor 20 from pre-stored data using a difference between an absorbance value acquired when light of a first wavelength is irradiated and an absorbance value acquired when light of a second wavelength is irradiated.

The light emitter 41 may irradiate the light of the first wavelength and the light of the second wavelength onto the thermochromic pigment accommodated in the reactor 20, and the light receiver 42 may convert the light of the first wavelength and the light of the second wavelength that has propagated through the thermochromic pigment into electrical signals, and then transfer the electrical signals to the controller 50.

The controller 50 may measure a first absorbance value of the thermochromic pigment corresponding to the light of the first wavelength and a second absorbance value of the thermochromic pigment corresponding to the light of the second wavelength, based on the received electrical signals. Also, the controller 50 may calculate a difference between the first absorbance value and the second absorbance value, and determine a temperature of the reactor 20 based on the difference between the first absorbance value and the second absorbance value.

Referring to FIG. 12, since the difference between the first absorbance value 4 AU and the second absorbance value 1.5 AU, measured by the test apparatus A, is 2.5 AU, the controller 50 may decide temperature of the reactor 20 corresponding to the absorbance difference of 2.5 AU with respect to the test apparatus A, as 35° C., based on data stored in advance in the memory 60.

Although the test apparatus A and the test apparatus B measure different absorbance values for light of the same wavelength due to the structural deviation when the temperature of the reactor 20 of the test apparatus A is the same as that of the reactor 20 of the test apparatus B, a difference between the absorbance value for the first wavelength and the absorbance value for the second wavelength with respect to the test apparatus A may be identical to a difference between the absorbance value for the first wavelength and the absorbance value for the second wavelength with respect to the test apparatus B.

Accordingly, referring to FIG. 13, since the difference between the first absorbance value 4.5 AU and the second absorbance value 2 AU, measured by the test apparatus B, is 2.5 AU, the controller 50 may decide temperature of the reactor 20 corresponding to the absorbance difference of 2.5 AU with respect to the test apparatus B, as 35° C., based on data stored in advance in the memory 60.

As a result, the problem described above with reference to FIG. 8 can be resolved so that the temperature of the reactor 20 included in the test apparatus A and the temperature of the reactor 20 included in the test apparatus B can be determined as the same value in correspondence to the same absorbance difference.

Figure 14:
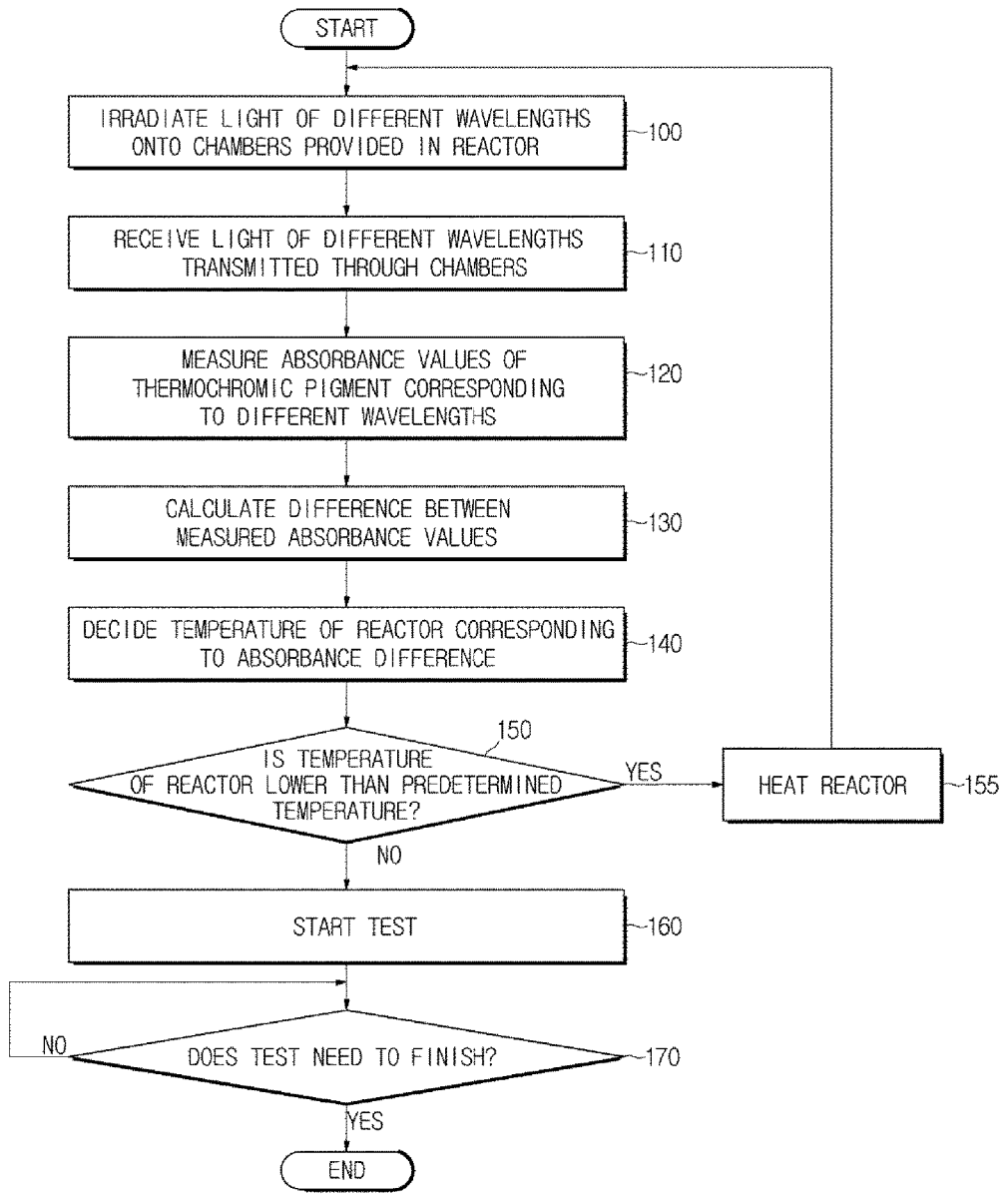
FIG. 14 is a flowchart illustrating a method for controlling a test apparatus, according to an exemplary embodiment.

FIG. 14 is a flowchart illustrating a method for controlling a test apparatus, according to an exemplary embodiment.

Referring to FIGS. 9 and 14, the light emitter 41 may irradiate light of different wavelengths onto the pigment chambers 22 provided in the reactor 20, in operation 100. A thermochromic pigment may be accommodated in the pigment chambers 22, and the light emitter 41 may irradiate light of a first wavelength and light of a second wavelength under the control of the controller 50. The plurality of light emitters 41 may irradiate light simultaneously, or one of the plurality of light emitters 41 may irradiate light sequentially. Details about the light of the first wavelength and the light of the second wavelength have been described above, and accordingly further descriptions thereof will be omitted.

Also, as described above, before light is irradiated toward the reactor 20, the controller 50 may raise the temperature of the thermochromic pigment accommodated in the reactor 20 until the temperature of the thermochromic pigment is higher than a predetermined temperature, and then lower the temperature of the thermochromic pigment to its original temperature.

The light receiver 42 may receive the light of different wavelengths that propagates through the thermochromic pigment accommodated in the pigment chambers 22, in operation 110, convert the received light of different wavelengths into electrical signals required for measuring absorbance values, and then transfer the electrical signals to the controller 50.

The controller 50 may measure absorbance values of the thermochromic pigment corresponding to the different wavelengths, based on the electrical signals received from the light receiver 42, in operation 120. More specifically, the controller 50 may measure a first absorbance value in correspondence to the light of the first wavelength that has propagated through the thermochromic pigment, and measure a second absorbance value in correspondence to the light of the second wavelength that has propagated through the thermochromic pigment.

Then, the controller 50 may calculate a difference between the first absorbance value and the second absorbance value, in operation 130, and determine a temperature of the reactor 20 based on the difference between the first absorbance value and the second absorbance value, in operation 140. That is, the controller 50 may compare a difference between the first absorbance value and the second absorbance value to data stored in advance in the memory 60 in order to determine the temperature of the reactor 20 according to the absorbance difference.

The controller 50 may compare the temperature of the reactor 20 to data about a predetermined temperature stored in advance in the memory 60, in operation 150. If the controller 50 determines that the temperature of the reactor 20 is lower than the predetermined temperature, the controller 50 may control the heater 70 to heat the reactor 20 until the temperature of the reactor 20 reaches the predetermined temperature, in operation 155. That is, the controller 50 may compare the temperature of the reactor 20 to data about an appropriate temperature for the reactor 20, and control the heater 70 according to the result of the comparison so that the temperature of the reactor 20 reaches the appropriate temperature or is within an appropriate temperature range.

If the controller 50 determines that the temperature of the reactor 20 is identical to the predetermined temperature, the controller 50 may control the test apparatus 100 to start a predetermined test, in operation 160. After the predetermined test is performed, the controller 50 may determine whether the predetermined test needs to be finished, in operation 170, and if the controller 50 determines that the predetermined test needs to be finished, the controller 50 may finish the predetermined test.

Figure 15:
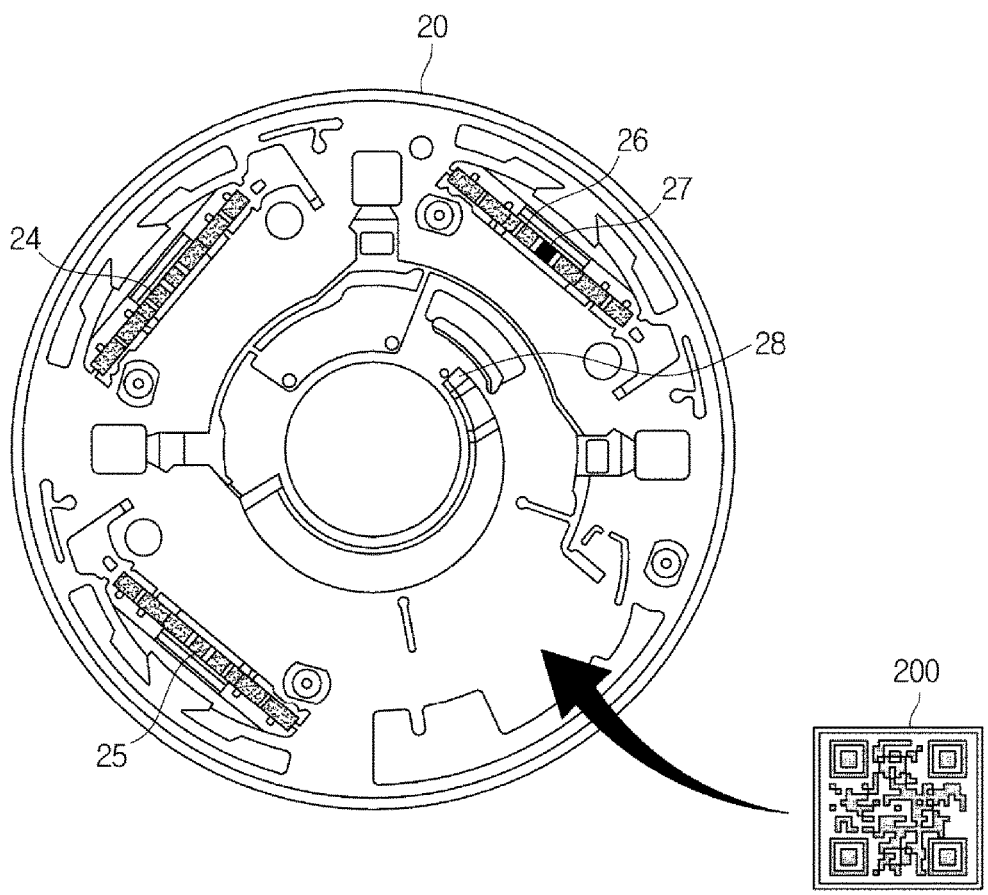
FIG. 15 shows the outer appearance of a reactor, according to another exemplary embodiment.

FIG. 15 shows the outer appearance of a reactor, according to another exemplary embodiment.

FIG. 15 shows a disc type reactor 20 according to another exemplary embodiment, which is different from the reactor 20 described above with reference to FIG. 4.

The reactor 20 shown in FIG. 15 may be a strip type reactor 20. In the strip type reactor 20, blood collected from a patient may be injected into the inside of the reactor 20 through an inlet hole 28 of a disc for a blood test, and the injected blood may spread into one or more strips 24, 25, and 26 included in the disc for the blood test. The test apparatus 100 may precisely analyze the blood existing in the strips 24, 25, and 26 included in the reactor 20.

A thermochromic pigment may be formed in the form of a lateral flow strip in the reactor 20. In particular, the reactor 20 may include a pigment strip 27 to accommodate a thermochromic pigment, and the temperature of the reactor 20 may be determined based on an absorbance value of the thermochromic pigment accommodated in the pigment strip 27. A method for determining a temperature of the reactor 20, as described above with reference to FIG. 15, is the same as the method described above with reference to FIGS. 4 to 14, and accordingly, further descriptions thereof will be omitted.

The reactor 20 may include identification information 200 including information about the temperature of the reactor 20. The identification information 200 may be a Quick Response (QR) code as shown in FIG. 15, and attached on the front surface of the reactor 20. Also, the identification information 200 may be formed in a format including at least one of a barcode, text data, a data matrix, a recognition pattern, Near Field Communication (NFC), and Radio Frequency Identification (RFID), and attached on the reactor 20.

If the reactor 20 is inserted into the test apparatus 100, the test apparatus 100 may recognize the identification information 200 attached on the reactor 20 in order to acquire data about an appropriate temperature of the reactor 20 for a predetermined test. If temperature of the reactor 20 is decided according to the above-described method, the test apparatus 100 may compare the temperature of the reactor 20 to the data about the appropriate temperature included in the identification information 200.

Also, the identification information 200 may include information related to the operations and control of the test apparatus 100, which can be stored in the memory 600.

In particular, data about a wavelength of light irradiated from the light emitter 41 may be stored in the identification information 200, and when the reactor 20 is inserted into the test apparatus 100, the controller 50 can select light to be irradiated, based on the data stored in the identification information 200.

Also, the identification information 200 may include absorbance data for light that has propagated through the thermochromic pigment accommodated in the pigment chambers 22 or the pigment strip 27 of the reactor 20. Also, the identification information 200 may include information about a first absorbance value and a second absorbance value of the thermochromic pigment corresponding to the light of the first wavelength and the light of the second wavelength that has propagated through the pigment chambers 22 or the pigment strip 27. Also, the identification information 200 may include data about temperature of the reactor 20 corresponding to a difference between the first absorbance value and the second absorbance value.

The identification information 200 may be included in various kinds of reactors 20, as well as the disc type reactor 20 shown in FIG. 15.

According to the exemplary embodiments as described above, by reducing temperature variation due to the mechanical deviation of the test apparatus, it is possible to accurately measure and control temperature of the reactor in which a thermochromic pigment is accommodated, resulting in an increase in accuracy of test results.

The test apparatus and the control method thereof have been described based on the above-described exemplary embodiments with reference to the accompanying drawings. However, the test apparatus and the control method thereof are not limited to the above-described exemplary embodiments, and the above-described exemplary embodiments are merely exemplary in all aspects. Although a few exemplary embodiments have been shown and described, it will be appreciated by those of ordinary skill in the art that changes may be made in these exemplary embodiments without departing from the principles and spirit of the present disclosure, the scope of which is defined in the claims and their equivalents.

What is claimed is:

1. A test apparatus for measuring a temperature of a reactor including a chamber in which a thermochromic pigment is accommodated, the test apparatus comprising:
    at least one light emitter configured to irradiate light of different wavelengths onto the chamber included in the reactor;
    a light receiver configured to receive the light of the different wavelengths that propagates through the chamber; and
    a controller configured to measure absorbance values of the thermochromic pigment in correspondence to the different wavelengths of the light received by the light receiver, to calculate at least one difference between a respective pair of the measured absorbance values, and to determine the temperature of the reactor based on the calculated at least one difference.

2. The test apparatus according to claim 1, wherein the at least one light emitter is further configured to irradiate light of a first wavelength and light of a second wavelength, and
    wherein the second wavelength is longer than the first wavelength.

3. The test apparatus according to claim 2, wherein the controller is further configured to measure a first absorbance value of the thermochromic pigment with respect to the irradiated light of the first wavelength, and
    to measure a second absorbance value of the thermochromic pigment with respect to the irradiated light of the second wavelength.

4. The test apparatus according to claim 3, wherein the controller is further configured to calculate a difference between the first absorbance value and the second absorbance value.

5. The test apparatus according to claim 4, wherein the controller is further configured to determine the temperature of the reactor based on the calculated difference between the first absorbance value and the second absorbance value.

6. The test apparatus according to claim 1, wherein when the determined temperature of the reactor is lower than a predetermined temperature, the controller is further configured to heat the reactor until the temperature of the reactor reaches the predetermined temperature.

7. The test apparatus according to claim 1, further comprising a heater configured to heat the reactor.

8. The test apparatus according to claim 1, further comprising a memory configured to store data that relates to the temperature of the reactor in correspondence with the calculated at least one difference between the respective pair of absorbance values.

9. The test apparatus according to claim 7, wherein the controller is further configured to heat the reactor until the temperature of the reactor is higher than a predetermined temperature, and when the temperature of the reactor becomes higher than the predetermined temperature, the controller is further configured to stop heating the reactor.

10. A method for controlling a test apparatus, the method comprising:
    irradiating light of different wavelengths onto a chamber provided in a reactor;
    receiving the light of the different wavelengths that propagates through the chamber;
    measuring absorbance values of a thermochromic pigment in correspondence to the different wavelengths of the received light;
    calculating at least one difference between a respective pair of the measured absorbance values; and
    determining a temperature of the reactor based on the calculated at least one difference.

11. The method according to claim 10, wherein the irradiating of the light of the different wavelengths comprises irradiating light of a first wavelength and light of a second wavelength, the second wavelength being longer than the first wavelength.

12. The method according to claim 11, wherein the measuring of the absorbance values of the thermochromic pigment comprises:
- measuring a first absorbance value of the thermochromic pigment in correspondence to the irradiated light of the first wavelength; and
- measuring a second absorbance value of the thermochromic pigment in correspondence to the irradiated light of the second wavelength.

13. The method according to claim 12, wherein the calculating of the at least one difference between the respective pair of the measured absorbance values comprises calculating a difference between the first absorbance value and the second absorbance value.

14. The method according to claim 13, wherein the determining of the temperature of the reactor comprises determining the temperature of the reactor based on the calculated difference between the first absorbance value and the second absorbance value.

15. The method according to claim 10, further comprising when the determined temperature of the reactor is lower than a predetermined temperature, heating the reactor until the temperature of the reactor reaches the predetermined temperature.

16. The method according to claim 10, further comprising heating the reactor.

17. The method according to claim 16, further comprising heating the reactor until the temperature of the reactor is higher than a predetermined temperature, and transmitting a control signal for stopping heating the reactor when the temperature of the reactor becomes higher than the predetermined temperature.

* * * * *